(12) United States Patent
Bauer et al.

(10) Patent No.: US 8,142,843 B2
(45) Date of Patent: Mar. 27, 2012

(54) AEROGEL PARTICLES AND METHODS OF MAKING SAME

(75) Inventors: Ulrich Bauer, Taunus (DE); Michael S. Darsillo, Landenberg, PA (US); Rex J. Field, Worms (DE); Joachim K. Floess, Urbana, IL (US); Jens Fründt, Hessen (DE); Stephane Rouanet, Westford, MA (US); Dhaval A. Doshi, Lexington, MA (US)

(73) Assignee: Cabot Corporation, Boston, MA (US)

( * ) Notice: Subject to any disclaimer, the term of this patent is extended or adjusted under 35 U.S.C. 154(b) by 824 days.

(21) Appl. No.: 12/048,857

(22) Filed: Mar. 14, 2008

(65) Prior Publication Data

US 2008/0311398 A1    Dec. 18, 2008

Related U.S. Application Data

(60) Provisional application No. 60/918,343, filed on Mar. 16, 2007.

(51) Int. Cl.
*B21D 39/00* (2006.01)
(52) U.S. Cl. ......... 427/212; 428/403; 428/407; 106/600
(58) Field of Classification Search .......... 428/402–407; 427/212; 106/600
See application file for complete search history.

(56) References Cited

U.S. PATENT DOCUMENTS

| | | | |
|---|---|---|---|
| 3,538,008 A * | 11/1970 | Ancel et al. ................... | 510/195 |
| 4,873,218 A | 10/1989 | Pekala | |
| 5,086,085 A | 2/1992 | Pekala | |
| 5,232,169 A | 8/1993 | Kaneko et al. | |
| 5,522,558 A | 6/1996 | Kaneko | |
| 5,827,363 A * | 10/1998 | Darsillo et al. ................ | 106/484 |
| 5,948,482 A | 9/1999 | Brinker et al. | |
| 6,126,097 A | 10/2000 | Chen et al. | |
| 6,145,765 A | 11/2000 | Capelle, Jr. et al. | |
| 6,598,283 B2 * | 7/2003 | Rouanet et al. .............. | 29/455.1 |
| 7,635,411 B2 * | 12/2009 | Rouanet et al. ................ | 106/600 |
| 2007/0037903 A1 * | 2/2007 | Swift ............................. | 523/218 |

FOREIGN PATENT DOCUMENTS

| WO | WO 94/25149 | | 11/1994 |
|---|---|---|---|
| WO | WO00/02734 | * | 1/2000 |
| WO | WO00/02734 A1 | | 1/2000 |
| WO | WO 00/56486 | | 9/2000 |

OTHER PUBLICATIONS

LeCaer et al., "Mechanical Alloying and High-Energy Ball-Milling: Technical Simplicity and Physical Complexity for the Synthesis of New Materials," five pages, (Date Unknown).

Zoz et al., "Processing of Ceramic Powder Using High Energy Milling," twelve pages, (Date Unknown).

* cited by examiner

*Primary Examiner* — Leszek Kiliman

(57) ABSTRACT

Aerogel particles having a mean particle size less than 1 micron, products containing the same, processes of making the same, and uses thereof are described. A process of making the particle is also described wherein starting aerogel particles are homogenized or wet milled. The starting aerogel particles can be surface treated during the milling process to prevent agglomeration or aggregation. The aerogel particles can be used in a variety of products and applications.

19 Claims, 1 Drawing Sheet

AEROGEL PARTICLES AND METHODS OF MAKING SAME

This application claims the benefit under 35 U.S.C. §119 (e) of prior U.S. Provisional Patent Application No. 60/918, 343, filed Mar. 16, 2007, which is incorporated in its entirety by reference herein.

BACKGROUND OF THE INVENTION

The present invention relates to aerogel particles, products containing the same, processes of making the same, and uses thereof.

Aerogel particles can have a very low density, high porosity, and small pore diameters. They can be extremely light weight and are usually formed by replacing the particles in a gel with a gas. Aerogel particles have a wide range of uses. For example, aerogels, in particular those with porosities of greater than about 60% and densities of less than about 0.4 g/cc, can exhibit very low thermal conductivity. Therefore, aerogels are used as thermal insulating materials as described, for example, in EP-A-0 171 722, incorporated in its entirety by reference herein. A class of aerogels includes silica gel particles. Silica gel materials are used in a wide variety of applications including matting agents, catalysts, personal care products, and chromatography to name a few.

Commercially produced silica gel materials can typically have large surface areas and void volumes and have narrow pore size distributions in the mesopore and micropore ranges. The lower limit of the particle size distribution of these materials is typically more than 3 microns which can be achieved by air jet milling of the dried silica gel powder. Thus, current processes do not permit the production of smaller particles, thereby limiting the use of silica gels or aerogels.

There is also a need to provide a tighter particle distribution range that can lead to better quality control of the finished product since each batch of material preferably has more similar physical properties.

Accordingly, there is a need for particles that avoid one or more of the above-described disadvantages.

SUMMARY OF THE PRESENT INVENTION

A feature of the present invention is to provide aerogel particles, such as hydrophobic aerogel particles, having a mean particle size of less than 1 micron.

Another feature of the present invention is to provide aerogel particles, such as hydrophobic aerogel particles, having a mean particle size of less than 1 micron wherein the aerogel particles can be silica gel particles or silica hydrosol particles.

Another feature of the present invention is to provide aerogel particles, such as hydrophobic aerogel particles, having at least 80% of the total particle size distribution less than 1 micron.

Another feature of the present invention is to provide aerogel particles, such as hydrophobic aerogel particles, having a mean particle size of from 0.1 micron to less than 1 micron.

To achieve these and other advantages, and in accordance with the purposes of the present invention, as embodied and broadly described herein, the present invention in part relates to aerogel particles, such as hydrophobic aerogel particles, having a mean particle size of less than 1 micron. The process of making the aerogel particles of the present invention can include milling starting aerogel particles. The starting aerogel particles can be milled or comminuted, for example, by wet milling, microfluidizer or sonication methods. Preferably, the starting aerogel particles are wet milled through a homogenizer or a ball mill. The starting aerogel particles can be treated in a solution comprising one or more agents that reduce or prevent agglomeration or reagglomeration during milling.

Another aspect of the present invention is to provide a process of making aerogel particles, such as hydrophobic aerogel particles, having a mean particle size of less than 1 micron comprising milling starting aerogel particles while attaching or coating at least one functional group to the starting aerogel particles. The functional group can be vinyl or a vinyl containing composition.

Another aspect of the present invention is to provide a process of making aerogel particles, such as hydrophobic aerogel particles, having a mean particle size of less than 1 micron, by sonication of a solution of aerogel starting particles. In one aspect, the sonication can be performed in the presence of a silylating agent, such as an organofunctional silane reactant, in the solution, wherein the silylating reagent will surface treat the aerogel particles, including fresh particle surfaces being exposed during and as a consequence of the sonication treatment, to make the resulting aerogel particles unreactive. In an alternative aspect, reactive sonicated aerogel particles are provided in a process of making aerogel particles in which silylating agent is not included or present during a sonication treatment performed on a solution of aerogel starting particles. The resulting reactive acrogel particles that are formed are capable of reacting with each other and/or other materials and can be used to form, for example, highly porous thin aerogel films. In another aspect sonication can be performed on a solution of aerogel particles where dry aerogel is used as a starting material in preparing the solution, such as in either the process in which sonication takes place in the absence of silylating agent or alternatively the process where it is present. The ability to use dry aerogel as a starting material in processes using sonication treatment increases production flexibility, amongst other advantages, yet still yields products with desirable characteristics and performance. The resultant solutions obtained from these various processes using sonication can be used as film-forming coating solutions either as is or as modified with viscosity adjusters, film thickness modifiers, catalysts, and so forth.

The present invention, in addition, relates to products containing the hydrophobic aerogel particles of the present invention. These products can be, but are not limited to, inks and coatings, an ink jet media coating, insulation, food products, absorbents, personal care products, a filler or a thickener, highly porous films, as well as other products.

Additional features and advantages of the present invention will be set forth, in part, in the description that follows, and, in part, will be apparent from the description, or may be learned by practice of the present invention. The objectives and other advantages of the present invention will be realized and attained by means of the elements and combinations particularly pointed out in the description and appended claims.

It is to be understood that both the foregoing general description and the following detailed description are exemplary and explanatory only, and are intended to provide a further explanation of the present invention, as claimed.

All patents, applications, and publications mentioned throughout the application are incorporated in their entirety by reference herein and form a part of the present application.

The accompanying drawing, which are incorporated in and constitute a part of this application, illustrate some of the embodiments of the present invention and together with the description serve to explain the principles of the present invention.

DETAILED DESCRIPTION OF THE PRESENT INVENTION

Figure 1:
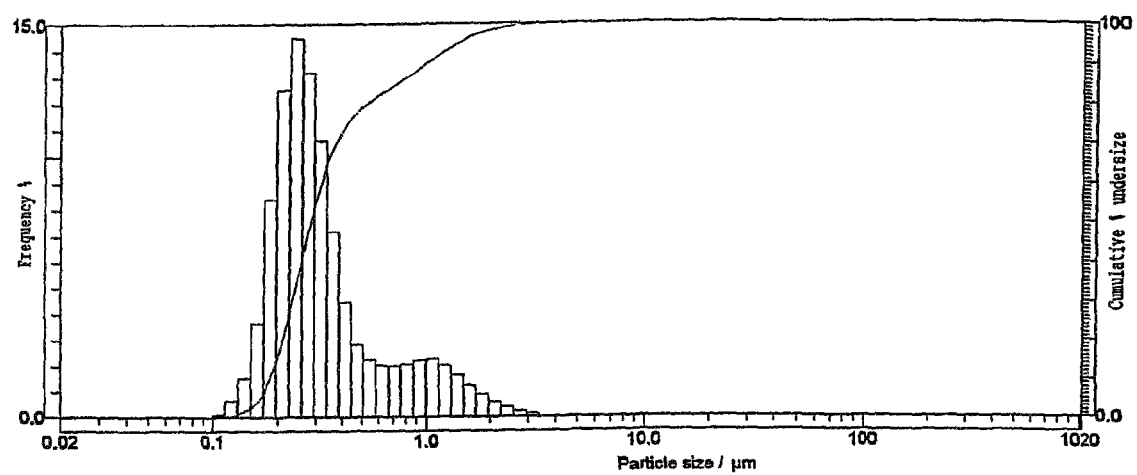
FIG. 1 is a graph of particle size distribution of aerogel particles according to one of the embodiments of the present invention.

The present invention in part relates to aerogel particles, such as hydrophobic aerogel particles. In one or more embodiments, the present invention relates to aerogel particles, such as hydrophobic aerogel particles, having a mean particle size of less than 1 micron. The aerogel particles can have a mean particle size of from 0.1 to less than 1 micron, or a mean particle size of from 0.25 micron to less than 1 micron, or a mean particle size of from 0.4 micron to less than 1 micron or a mean particle size of from 0.2 micron to 0.8 micron. The aerogel particles of the present invention can overcome many of the above-described disadvantages. The aerogel particles according to the present invention can be silica gel particles or silica hydrosol particles or other types of aerogel particles. In one or more embodiments, the aerogel particles can have a tight particle distribution range. For instance, the particle distribution range can be wherein at least 80% of the total particle size distribution is less than 1 micron, or wherein at least 90% of the total particle size distribution is less than 1 micron. Other particle distribution ranges are possible. The optional particle size distributions can be a characteristic in combination with the mean particle sizes of the present invention. The aerogel particles, such as hydrophobic aerogel particles, according to the present invention can be utilized in a number of applications such as an inks, coatings, ink jet media coatings, an inorganic thickener for aqueous based systems, a filler for reinforcement, a thickener for toothpastes, food products, personal care products, insulation materials, or any product of manufacture that can contain aerogel particles.

The starting aerogel particles can be wet milled (wet-milling is also referred to as wet-grinding) through a mill or homogenizer. In the preferred process of making the aerogel particles of the present invention, starting aerogel particles are milled, and preferably wet milled, meaning the particles are milled in a liquid or the particles are in a slurry. Any type of wet milling device can be used, such as an Attritor type mill, or ball mill. A high energy mill for a powder (or particles) dispersed in a fluid medium or optional milling media can be used. In general, any means of wet-milling can be used with an appropriate homogenizer. The wet milling fluid can be organic or aqueous liquid. The organic liquid or non-aqueous liquid is preferred when milling hydrophobic aerogel particles. The fluid medium (aqueous or non-aqueous) can be a surfactant or a surface-active organic agent. For example, the fluid can be a lubricating agent. The liquid used can also be water, alcohol, and the like. A milling media such as stainless steel balls, for example, can be used.

The starting aerogel particles, the fluid medium if any, and optional grinding media are combined in predetermined proportions. The volume of the starting aerogel particles and other reagents can be any amount, such as from about 1% to about 99%, preferably from about 10% to about 70% by volume.

The high-energy mill can be any high-energy mill, for example, a centrifugal mill, and preferably a commercially available planetary ball mill, for instance, from Glen Mills, Inc. or Retsch (e.g., PM 400). Other examples include jet mills, like a spinning air flow jet mill, or fluid energy mills, like an opposed jet fluid energy mill (e.g., from CCE Technologies, Inc.). Examples of mills are also set forth in U.S. Pat. Nos. 5,522,558; 5,232,169; 6,126,097; and 6,145,765; all incorporated in their entirety by reference herein. Preferably, the high-energy mill is rotated at a sufficient speed so as to impart a high impact force of from about 0.3 G to about 25 G to the milling media and/or the powder. More preferably, the high-energy mill imparts a force of at least 0.5 G to the milling media and/or powder. For example, the high energy mill can be rotated at from about 100 to about 400 rpm or more, and is preferably rotated at least from about 300 rpm.

Grinding, for instance, can be achieved by using a planetary ball mill having a grinding chamber that includes a rotor shaft that is used to rotate grinding media. A high energy mill is also described in "Mechanical Alloying and High-Energy Ball-Milling: Technical Simplicity and Physical Complexity for the Synthesis of New Materials," by G. Le Caer, S. Begin-Colin, and P. Delcroix, which can be found at www.ademe.fr/recherche/manifestations/materiaux_2002/Site/file/pdf%5CCM01109.PDF, and in "Processing of Ceramic Powder Using High Energy Milling," by H. Zoz and H. Ren, which can be found at www.zoz.de/de/veroeff/19.htm, both of which are incorporated in their entireties herein by reference. The milling balls can be accelerated by the rotating rotor, and collide with each other at a relative velocity of up to 14 m/s or more.

Milling for any of the high-energy mills can occur for any predetermined amount of time, and is preferably for a time of about 10 hours or less, such as from about 30 minutes to about 10 hours, e.g., from about 2 to about 3 hours. The particle size and/or BET surface areas of the particles produced generally can relate to milling times.

The milling can also be done in an Attritor mill such as a 1 S mill which is operated at about 350 rpms. When the milling is completed, the mixture can then be subjected to a heat treatment as described above. For purposes of the present invention, any of the milling steps described in the present application can be conducted under heat, such as described in International Published PCT Patent Application No. WO 00/56486 incorporated in its entirety by reference herein. Also other additives can be added during any milling step, such as a lubricant, surfactant, dispersant, solvent, or the like as described above.

Another homogenizer that can be used is a microfluidizer available from Microfluidics International Corporation. This technology utilizes a constant pressure intensifier pump which can reproducibly pressurize the suspension or dispersion, for instance, to 25,000 psi. Following pressurization, the suspension enters an interaction chamber which allows it to be fed through minute microchannels at speeds up to hundreds of meters per second. The process stream then separates into two, changes direction, and collides with itself into a single stream. The particles in the suspension, such as silica gel particles, are acted upon by three primary forces, shear, impact and cavitation, resulting in production of submicron particles according to the present invention.

Briefly, the operating principles in a microfluidizer, more specifically, the M-110EH microfluidizer available from Microfluidics International Corporation, is as follows. Power for this microfluidizer is generated by an on-board hydraulic power system, which supplies pressurized hydraulic oil to a single-acting intensifier pump. The intensifier pump amplifies the hydraulic pressure and transfers it into liquid pressure in the process stream. Working pressure levels as high as 25,000 psi can be reached. During the suction stroke, the intensifier pump draws product from the inlet reservoir into the pressure chamber via the inlet check valve, which closes during the power stroke. During the power stroke, the product stream is elevated to a constant pressure level. The pressurized product stream then enters the interaction chamber and passes through geometrically fixed microchannels, causing it to accelerate to very high velocities. It is here where three primary forces bring about the desired results of the product. First is a shear force which is deformation of the product stream, occurring in contact with channel walls at high velocity. Second is an impact force which is based on collision, occurring when the high impact velocity product stream impinges upon itself. Third is cavitation, which is the formation and collapse of cavities within the product stream. Upon exiting the interaction chamber, the product is further processed as it passes through an auxiliary processing module. A heat exchanger returns the product stream to ambient temperature.

Another method of providing energy of communition (milling) is to subject a solution of aerogel to a sonication treatment. The sonic energy breaks the aerogel particles into smaller fragments. Sonication can be used to form fine aerogel particles, such as those having a mean particle size of less than 1 micron or other sizes described herein, from larger aerogel particles. A sonic probe, such as available as model MisoNix Sonicator® 3000 from Cole-Parmer Instrument Company, can be used for performing sonication, operating, for example, at 20 kHz maximum frequency, and 550 W maximum power. Time of sonication, frequency and power used, for example, impact the end particle size distribution. A typical process in accordance with embodiments of the present invention using sonication can include taking the aerogel particles into a solution of solvent(s) and reactant(s) if used. In one aspect, the use of reactants, such as silylating agents and organofunctional silanes in particular, provides treatment of the newly generated aerogel particle surfaces created during sonication of the starting aerogel particles. This yields unique unreactive aerogel particles. Alternatively, in another aspect, if reactive milled particles are required or desired, then the silane treating agent and alcohols are not added during sonication. Sonication of the dry starting aerogel particles can be performed with a nonpolar solvent such as toluene or hexane. Reactive milled particles are of interest because they especially can be utilized to form thin films.

The solution that is subjected to sonication can comprise, for example, a siloxane, such as hexamethyldisiloxane (HMDS), one or more acid(s), e.g HCl, IDA, a silane, such as trimethylalkoxysilane, ammonia, an alcohol, like ethanol, a silazane, such as hexamethyldisilazane (HMDZ), chlorosilane, alkoxysilane, or combinations thereof. The solution can comprise a mixture of HCl, IDA, and HMDS; or trimethylalkoxysilane, ammonia, and water; or HMDZ and water; or ethanol, HMDS, ammonia and water; or chlorosilane and water. The solution can treat at least a portion of the surface of the starting aerogel particle and/or newly generated surfaces created during milling and thereby prevent or reduce agglomeration or aggregation during milling as the size of the starting aerogel particles are simultaneously decreased.

It is also advantageous from a cost and flexibility point of view to be able to use already prepared (dry) aerogel particles to make similar thin films. That is, sonication can be performed on a solution of aerogel particles where dry aerogel is used as a starting material in preparing the solution, such as in either the process in which sonication takes place in the absence of silylating agent or alternatively the process where it is present. The ability to use dry aerogel as a starting material in processes using sonication treatment increases production flexibility, amongst other advantages, yet still yields products with desirable characteristics and performance. A non-limiting example of dry aerogels are Nanogel® aerogels, such as Nanogel® TLD 201. A non-limiting exemplary process using dry aerogel as starting material can be the following: (1) addition of an alcoholic solvent such as ethanol/isopropanol to dry hydrophobic aerogel particles (such as Nanogel®); (2) optional addition of a second solvent, such as toluene or hexane; (3) sonication of the resultant viscous gel like material for a duration such that a low viscosity solution is formed (e.g., 1 g dry aerogel/15 cc ethanol at 1 hr. at 20 kHz using MisoNix Sonicator® 3000); (4) optional addition of a third solvent, such as toluene, alcohol to adjust the viscosity and coating thickness; (5) optional addition of small (catalytic) amount of acid or base (e.g., $NH_4OH$); and (6) use of the resultant solution to coat a substrate with methods known in the art, such as dip coating, spin coating, drain coating, and so forth. The resultant solutions obtained from these various processes using sonication can be used as film-forming coating solutions either as is or as modified with viscosity adjusters, film thickness modifiers, catalysts, and so forth.

There is no restriction on the homogenizer apparatus for the process of making the aerogel particles according to the present invention. Any homogenizer or mill known for this purpose to a person skilled in the art can be used.

The starting aerogel particles can be treated in a solution comprising one or more agents that prevent or reduce reagglomeration during milling. Generally, the treatment involves at least partially coating the particles or creating a slurry or solution with the agent(s) and particles present. The liquid used for wet milling can have a dual purpose, that is, act as the wet milling medium and also act as an agent to reduce or prevent re-agglomeration of the pre-milled and milled particles during milling. The solution can comprise a siloxane, like hexamethyldisiloxane (HMDS), one or more acid (s), iminodiacetic acid (IDA), a silane, like trimethylalkoxysilane, ammonia, an alcohol, like ethanol, a silazane, like hexamethyldisilazane (HMDZ), chlorosilane, or combinations thereof. The solution can comprise a mixture of HCl, IDA, and HMDS; or trimethylalkoxysilane, ammonia, and water; or HMDZ and water; or ethanol, HMDS, ammonia and water; or chlorosilane and water. The solution can treat at least a portion of the surface of the starting aerogel particle and/or newly generated surfaces created during milling and thereby prevent or reduce agglomeration or aggregation during milling as the size of the starting aerogel particles are simultaneously decreased. Additionally, during the milling process, at least one functional group can be attached or coated onto the starting aerogel particles. Preferably, the at least one functional group is vinyl.

In the present invention, the terms "aerogel particles" and "aerogels" are used interchangeably. Any aerogel particles can be used in the present invention. The preferred aerogel particles for use in the present invention are those that are based on metal oxides that are suitable for a sol-gel technique (C. J. Brinker, G. W. Scherer, Sol-Gel Science. 1990, Chaps. 2 and 3), such as Si or Al compounds, or those based on organic substances that are suitable for the sol-gel technique, such as melamine-formaldehyde condensates (U.S. Pat. No. 5,086,085) or resorcinol-formaldehyde condensates (U.S. Pat. No. 4,873,218). They can also be based on mixtures of the above-mentioned materials. Preferably, aerogels containing silicon (Si) compounds and, more preferably, $SiO_2$ are used. Thus, the preferred starting aerogel particles according to the present invention are silica gel particles or silica hydrosol particles. To reduce the radiative contribution to thermal conductivity, the aerogel can contain IR opacifiers, such as carbon black, titanium dioxide, iron oxide, or zirconium dioxide, or mixtures thereof.

The starting aerogel particles can have various particle sizes and/or particle size distributions. Generally, the starting aerogel particle has a mean particle size of 1 micron or higher, such as 3 microns or higher, or from 3 microns to 3 mm. The starting aerogel particles can be in the form of comminuted powders or larger chunks. These particles can be in the shape of spheres, although the aerogel chunks can have any shape.

Essentially, any commercially available aerogel can be used in the present invention as the starting aerogel particles. These aerogels can be hydrophobic. Examples include, but are not limited to, aerogels commercially available from Cabot Corporation. Particular commercially available types include, but are not limited to, Nanogel® aerogels.

The starting aerogel particles used in the present invention can have hydrophobic surface groups. In order to avoid any subsequent collapse of the aerogels by the condensation of moisture within the pores, it is preferred that hydrophobic groups be covalently bonded on at least the inside surface of the aerogel. Preferred groups for permanent hydrophobization are mono-, di-, or tri-substituted silyl groups of the formulas:

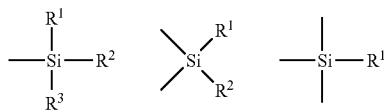

where $R^1$ is hydrogen or a non-reactive linear, branched, cyclic, aromatic, or heteroaromatic organic radical, preferably, a linear, branched, or cyclic $C_6$-$C_{18}$-alkyl radical or a $C_6$-$C_{14}$-aryl radical. $R^2$ and $R^3$, which can be the same or different, can be hydrogen or a non-reactive linear, branched, cyclic, aromatic, or heteroaromatic organic radical, preferably, a linear, branched, or cyclic $C_1$-$C_{18}$-alkyl radical, a $C_6$-$C_{14}$-aryl radical, an OH or OR' group, wherein R' is a linear or branched $C_1$-$C_6$-alkyl radical; preferably trialkyl and/or triarylsilyl groups. $R^1$, $R^2$, and $R^3$, which can be the same or different, can be $C_1$-$C_6$-alkyl, cyclohexyl, or phenyl.

The use of trimethyl- and dimethylsilyl groups for permanent hydrophobization of the aerogel can be used. These groups can be introduced as described in WO 94/25149 (incorporated in its entirety by reference herein) or by gas-phase reaction between the aerogel and, for example, an activated trialkylsilane derivative, such as a chlorotrialkylsilane or a hexaalkyldisilazane (cf. R. Iler, The Chemistry of Silica, Wiley & Sons, 1979).

Furthermore and within certain limits, the thermal conductivity of the aerogels can decrease as porosity increases and density decreases. For this reason, aerogels with porosities of greater than about 60% and densities of less than about 0.4 g/cc are preferred. More preferably, the aerogels of the present invention have densities of from about 0.05 to about 0.15 g/cc. The thermal conductivity of the aerogel particles can be less than about 40 mW/m° K., preferably, less than about 25 mW/m° K., and, more preferably, the thermal conductivity of the aerogel particles is from about 12 to about 18 mW/m° K., or lower.

As stated above, the starting aerogel particles of the present invention can be hydrophobic and/or have hydrophobic surface groups. Hydrophobic aerogel particles cannot be wetted by water alone and, therefore, wet milling of hydrophobic particles in aqueous solution could be difficult. In general, when hydrophobic aerogel particles are added to water they simply float on the surface, even under vigorous agitation. In order to achieve a homogeneous distribution of the hydrophobic aerogel particles in an aqueous slurry, at least one wetting agent, such as at least one surface active agent (e.g., surfactant), and/or at least one dispersant can be used to more easily permit the wetting of the hydrophobic aerogel particles with aqueous solutions, like water. The dispersant may be selected from ionic (anionic and cationic) surfactants, amphoteric surfactants, nonionic surfactants, high molecular surfactants, and high molecular compounds, for example. The anionic surfactants include alkyl sulfates and higher alkyl ether sulfates, more specifically, ammonium lauryl sulfate, and sodium polyoxyethylene lauryl ether sulfate, for example. The cationic surfactants include aliphatic ammonium salts and amine salts, more specifically, alkyl trimethylammonium, and polyoxyethylene alkyl amine, for example. The amphoteric surfactants may be of betain type, such as alkyl dimethyl betain, or of oxido type, such as alkyl dimethyl amine oxido, for example.

The nonionic surfactants include glycerol fatty acid ester, propylene glycol fatty acid ester, sorbitan fatty acid ester, polyoxyethylene sorbitan fatty acid ester, tetraoleic acid polyoxyethylene sorbitol, polyoxyethylene alkyl ether, polyoxyethylene alkyl phenyl ether, polyoxyethylene polyoxypropylene glycol, polyoxyethylene polyoxypropylene alkyl ether, polyethylene glycol fatty acid ester, higher fatty acid alcohol ester, polyhydric alcohol fatty acid ester, and others.

Typical wetting agents that can be used include, for example, AEROSOL OT (sodium di-2-ethylhexylsulfosuccinite), BARLOX 12i (a branched alkyldimethylamine oxide), TRITON 100 (octylphenoxypolyethoxy(9-10)ethanol), TWEEN surfactants like TWEEN 100 surfactant, and BASF pluronic surfactants. A general class is glycols, alkoxylates polyoxyalkylene fatty ethers, such as polyoxyethylene fatty ethers, sorbitan esters, mono and diglycerides, polyoxyethylene sorbitol esters, polymeric surfactants like Hypermen polymer surfactants, sodium coco-PG-dimonium chloride phosphate and coamidopropyl PG-dimonium chloride phosphate, phosphate esters, polyoxyethylene (POE) fatty acid esters, Renex nonionic surfactants (nonionic esters formed by reaction of ethylene oxide and unsaturated fatty acids and heterocyclic resin acids.), alcohol ethoxylates, alcohol alkoxylates, ethylene oxide/propylene oxide block copolymers, polyoxyethylene derivatives of sorbitan esters or combinations thereof. The preferred wetting agent is capable of volatilizing during the drying and/or hot calendaring to allow suitable recovery of the hydrophobicity of the hydrophobic aerogel particles. If the wetting agent remains on the surface of the aerogel particles, the remaining wetting agent can contribute to the overall thermal conductivity of the composite material. Thus, the preferred wetting agent is one that is removable, such as by volatilization with or without decomposition or other means. Generally, any wetting agent that is compatible with the aerogel can be used.

In general, hydrophobic aerogel particles can include a large surface area, such as, for example, about 700 m²/g. Accordingly, the amount of surfactant or dispersant that would allow complete wetting of the aerogel may be large. Generally, complete wetting is considered to take place when a sufficient amount of wetting agent has been added to allow the water to penetrate the interior of the aerogel particles so that they sink in the aqueous medium. Typically, the addition of more than about 0.6 to 0.8 parts by wt. wetting agent to about 1 part by wt. aerogel can result in full wetting of the hydrophobic aerogel particles. However, when the aqueous slurry is substantially dried, the fully wetted particles can exhibit a large increase in particle bulk density. As a consequence, the thermal conductivity of a composite material made with fully wetted aerogel particles tends to have higher thermal conductivities.

In order to satisfactorily recover the hydrophobicity and low density of the hydrophobic aerogel particles, it is preferable to use an amount of wetting agent to only wet the outer surface layers of the hydrophobic aerogel particles. Thus, a sufficient amount of wetting agent can be present to be adsorbed on the outer surface of the aerogels particles. When the outer surface layers of the aerogel particles are only wetted, there may be a negligible increase in the bulk density of the aerogel particles on drying. As a consequence, the hydrophobicity of the hydrophobic aerogel particles is relatively unaffected and a composite material tends to have a low thermal conductivity. Thus, preferably about 0.6 parts by wt. or less wetting agent to about 1 part aerogel by wt. is used. For instance, 0.05 part to about 0.5 parts by wt. wetting agent can be used to about 1 part by wt. aerogel. The wetting agent can be pre-applied to the aerogel, or can be introduced into the slurry preferably prior to, at the same time, or after the aerogel is added.

The amount of wetting agent required to only cause the wetting of the outer surface layers of the aerogel particles can depend on the size of the hydrophobic aerogel particles. In general, particles of smaller size require more wetting agents. Preferably, the wetting agent is in an amount sufficient to allow substantial recovery of the hydrophobicity and low density of the hydrophobic aerogels after drying. More preferably, the wetting agent can be in an amount sufficient for the aerogel to have a thermal conductivity of less than about 40 mW/m° K., and, most preferably, to have a thermal conductivity of from about 10 to about 30 mW/m° K., such as from about 12 to about 25 mW/m° K.

Thus, the aerogel used to make the particles according to the invention has desirable properties attributed to the aerogel such as low density, low thermal conductivity, low electrical conductivity, low dielectric constant and/or shock absorption, and/or light transmission.

The coating process or surface treatment as described above can be performed before, during, and/or after the starting aerogel has undergone the milling process, depending on the properties of the particles that are desired. However, as described below, certain surface treatments are preferably performed during the milling process in order to prevent reagglomeration or aggregation of particles.

For example, an effect occurring during the micronization in an organic solvent is a significant increase in viscosity of the suspension which is undesirable. One preferred solvent is HMDS. The HMDS can be a hydrophobing agent. It is believed that this is due to the generation of the untreated oxidic surface on the aerogel particles, which leads to aggregation or reagglomeration of the particles.

The process according to the present invention can solve this problem by conducting two operations in essentially one process step. Milling of an aerogel suspension so as to generate submicron particles is performed at the same time as having reactive species available in the suspension in order to treat the new silica surface as it is generated. This keeps the viscosity of the suspension low, allows a narrow residence time distribution of all particles inside the mill, ensures a completely treated surface of the particles, and/or ensures that the submicron particles produced have similar properties as compared to the unmilled aerogel feed.

Other desirable properties of the aerogel or particles according to the present invention can be based on the surface area and/or void volume of the particles.

Additionally, an exemplary aerogel that can be used for the process of making the particles of the instant invention has a surface functionality of trimethyl silyl, has a surface area of 700 $m^2$/g, a tap density of 40 kg/$m^3$, an oil absorption in DBP of 540 $cm^3$/100 g, a median particle of 8 μm, a pH in 5% m/m suspension of 5, and is a white powder in form. An aerogel having these properties is the Nanogel® aerogel available from Cabot Corporation.

As indicated earlier, the starting aerogel particles can be silica gel particles or silica hydrosol particles. The starting aerogel particles can be in an aged silica gel suspension, as described herein.

The silica hydrosol can be prepared by fast addition of a diluted sodium silicate suspension to a rapidly stirring solution comprising an acid such as HCl. The rapidly stirring solution preferably has a pH in the range of about 5 to about 5.4, wherein a hydrogel is formed. The hydrogel is further broken up in a reaction mixture and the reaction mixture can be heated. The heating step is preferably performed under agitation. The reaction mixture is allowed to reflux for about 2.25 hours followed by cooling to about 40° C. This cooling step produces an aged silica gel suspension.

The aged silica gel suspension can have an approximate surface area of about 350 $m^2$/g (e.g., 100 $m^2$/g to 500 $m^2$/g) and a silica content of about 8% (e.g., 1% to 15%). The suspension can then be homogenized. The suspension can also be pressurized, such as at a pressure of 20,000 psi. During the homogenization process, the particles in the suspension can be subjected to forces such as shear, impact, cavitation, or combinations thereof. After the homogenizing step, the resulting hydrophobic aerogel particles can be dried.

Instead of preparing a silica gel suspension as described above, the starting aerogel particles can be obtained in other ways. For example, a dry aerogel can be dispersed in an organic solvent to produce an organogel suspension or obtaining a previously-undried suspension of organogel particles then wet milling the organogel suspension or the previously-undried suspension.

After milling, the fluid can be separated or removed from the particles by any process, such as air-drying, heating, filtering, evaporating, or combinations thereof. The fluid is preferably removed by heating at any temperature sufficient to generally prevent agglomeration and/or dry the particles.

Any preliminary or intermediate or final milling step can be used in addition to the milling steps described herein.

The present invention will be further clarified by the following examples, which are intended to be purely exemplary of the present invention.

EXAMPLES

Example 1

A sample of silica gel suspension was obtained from Cabot Corporation. The silica hydrosol was prepared by fast addition of a diluted sodium silicate suspension to a rapidly stirring solution comprising an acid such as HCl. The rapidly stirring solution had a pH in the range of about 5 to about 5.4, wherein a hydrogel was formed. The hydrogel was further broken up in a reaction mixture and the reaction mixture was heated. The heating step was performed under agitation. The reaction mixture was allowed to reflux for about 2.25 hours followed by cooling to about 40° C. This cooling step produced an aged silica gel suspension. The aged silica gel suspension had an approximate surface of about 350 $m^2$/g and a silica content of about 8%. The mean particle size of the aged silica suspension was 31 microns.

The sample was then subjected to a homogenizing process (wet milling) using the M-110EH microfluidizer available from Microfluidics International Corporation, as described above. The pressure achieved in the microfluidizer for this example was 10,000 psi and one pass through the microfluidizer was done.

FIG. 1 shows the data obtained from a laser scattering particle size distribution analyzer for this sample after it was homogenized. The size of the particles obtained ranges from 0.115 micron to 3.409 microns. The percent frequency of certain particle sizes are shown in Table 1 below.

TABLE 1

| Frequency (%) | Size (microns) |
|---|---|
| 0.14 | 3.409 |
| 0.25 | 2.976 |
| 0.40 | 2.599 |
| 0.62 | 2.269 |
| 0.91 | 1.981 |
| 1.27 | 1.729 |
| 1.66 | 1.510 |
| 2.03 | 1.318 |
| 2.28 | 1.151 |
| 2.23 | 1.005 |
| 2.08 | 0.877 |
| 2.03 | 0.766 |
| 2.05 | 0.669 |
| 2.25 | 0.584 |
| 2.84 | 0.510 |
| 4.47 | 0.445 |
| 7.19 | 0.389 |
| 10.63 | 0.339 |
| 13.20 | 0.296 |
| 14.50 | 0.2559 |
| 12.52 | 0.226 |
| 8.40 | 0.197 |
| 3.67 | 0.172 |
| 1.55 | 0.150 |
| 0.67 | 0.131 |
| 0.14 | 0.115 |

The median particle size was determined as 0.282 micron and the mean particle size was determined as 0.437 micron. In addition, about 90% of the particles are less than 1 micron in particle size.

Example 2

A treatment reagent system was prepared by combining trimethylalkoxysilane, ammonia and water. The reagent system was then mixed into a suspension of Nanogel® aerogel available from Cabot Corporation in HMDS. The suspension was then fed to a stirred-media mill.

As the viscosity increased, additional treatment reagent was added to the suspension. This provided an almost immediate chemical surface treatment to the aerogel particles thereby reducing the adhesion forces between the particle surfaces, because the viscosity of the suspension is decreased, giving benefits for the ongoing milling process. The milling gave a final product having a particle size distribution in the submicron range, having few or no particles larger than 1 micron.

Example 3

A treatment reagent system was prepared by combining hexamethyldisilazane (HMDZ) and water. The reagent system was then mixed into a suspension of Nanogel® aerogel available from Cabot Corporation in HMDS. The suspension was then fed to a stirred-media mill.

As the viscosity increased, additional treatment reagent was added to the suspension. This provided an almost immediate chemical surface treatment to the aerogel particles thereby reducing the adhesion forces between the particle surfaces, because the viscosity of the suspension is decreased, giving benefits for the ongoing milling process. The milling gave a final product having a particle size distribution in the submicron range, having few or no particles larger than 1 micron.

Example 4

A treatment reagent system was prepared by combining ethanol, HMDS, ammonia and water. The reagent system was then mixed into a suspension of Nanogel® aerogel available from Cabot Corporation in HMDS. The suspension was then fed to a stirred-media mill.

As the viscosity increased, additional treatment reagent was added to the suspension. This provided an almost immediate chemical surface treatment to the aerogel particles thereby reducing the adhesion forces between the particle surfaces, because the viscosity of the suspension is decreased, giving benefits for the ongoing milling process. The milling gave a final product having a particle size distribution in the submicron range, having few or no particles larger than 1 micron.

Example 5

A sample of silica gel particles is obtained. The silica gel is mixed with HCl, IDA and HMDS and wet milled in a homogenizer. By milling while treating the silica gel, it was found that the size of the aerogel particles was decreased while simultaneously preventing reagglomeration.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of making aerogel particles having a mean particle size of less than 1 micron comprising milling starting aerogel particles and treating the starting aerogel particles in a solution comprising one or more agents that prevent agglomeration during milling to form milled aerogel particles, and then drying said milled aerogel particles to obtain dried aerogel particles in an unagglomerated state, wherein the starting aerogel particles and the dried aerogel particles are hydrophobic aerogel particles, and wherein the dried aerogel particles have a thermal conductivity of less than about 40 mW/m° K.

2. The method of claim 1, wherein the starting aerogel particles are milled through a homogenizer.

3. The method of claim 1, wherein the milling is wet milling.

4. The method of claim 3, wherein said wet milling occurs in an organic liquid.

5. The method of claim 3, wherein said wet milling occurs in an aqueous liquid.

6. The method of claim 1, wherein the solution comprises hexamethyldisiloxane (HMDS).

7. The method of claim 4, wherein the particle size of the starting aerogel particles is decreased while simultaneously preventing agglomeration.

8. The method of claim 6, further comprising at least one acid, and IDA.

9. The method of claim 1, wherein the starting aerogel particles is silica hydrosol.

10. The method of making the aerogel particles of claim 1, wherein the solution comprises trimethylalkoxysilane, hexamethyldisilazane (HMDZ), chlorosilane, and optionally containing an alcohol, ammonia, or both.

11. The method of claim 1, wherein, as part of said treating, at least one functional organic group is attached to the starting aerogel particles.

12. The method of making the aerogel particles of claim 11, wherein the at least one functional organic group is vinyl.

13. The method of claim 1, wherein the aerogel particles are hydrophobic aerogel particles.

14. A method of making aerogel particles having a mean particle size of less than one micron comprising sonicating a solution comprising starting aerogel particles in the presence of a silylating agent to form said aerogel particles having said mean particle size to form milled aerogel particles, and then drying said milled aerogel particles to obtain dried aerogel particles in an unagglomerated state, wherein the starting aerogel particles and the dried aerogel particles are hydrophobic aerogel particles, and wherein the dried aerogel particles have a thermal conductivity of less than about 40 mW/m° K.

15. A method of making aerogel particles having a mean particle size of less than one micron comprising sonicating a solution comprising dry starting aerogel particles and solvent, in the absence of a silylating agent to form said aerogel particles having said mean particle size to form milled aerogel particles, and then drying said milled aerogel particles to obtain dried aerogel particles in an unagglomerated state, wherein the starting aerogel particles and the dried aerogel particles are hydrophobic aerogel particles, and wherein the dried aerogel particles have a thermal conductivity of less than about 40 mW/m° K.

16. The method of claim 15, further comprising forming a porous thin aerogel film from said aerogel particles.

17. The method of claim 1, wherein said solution treats at least a portion of a surface of said starting aerogel particles or treats newly generated surfaces of said aerogel particle during said milling, or both.

18. The method of claim 1, wherein said starting aerogel particles are treated with at least one wetting agent.

19. The method of claim 1, wherein said solution comprises at least one hydrophobing agent.

* * * * *